(12) United States Patent
Bientinesi et al.

(10) Patent No.: US 8,188,290 B2
(45) Date of Patent: May 29, 2012

(54) PROCESS FOR PREPARING N, N-SUBSTITUTED CARBAMOYL HALIDES

(75) Inventors: Ilaria Bientinesi, Verona (IT); Zadeo Cimarosti, Verona (IT); Giuseppe Guercio, Verona (IT); Corinne Leroi, Verona (IT); Alcide Perboni, Verona (IT)

(73) Assignee: Glaxo Group Limited, Middlesex (GB)

( * ) Notice: Subject to any disclaimer, the term of this patent is extended or adjusted under 35 U.S.C. 154(b) by 959 days.

(21) Appl. No.: 12/091,591

(22) PCT Filed: Oct. 26, 2006

(86) PCT No.: PCT/EP2006/010437
§ 371 (c)(1),
(2), (4) Date: Apr. 25, 2008

(87) PCT Pub. No.: WO2007/048642
PCT Pub. Date: May 3, 2007

(65) Prior Publication Data
US 2008/0262234 A1    Oct. 23, 2008

(30) Foreign Application Priority Data

Oct. 28, 2005 (GB) .................................. 0522061.1

(51) Int. Cl.
*C07D 211/06* (2006.01)
*C07C 69/76* (2006.01)
(52) U.S. Cl. ........................................ 546/245; 560/111
(58) Field of Classification Search .................. 546/245; 560/111
See application file for complete search history.

(56) References Cited

U.S. PATENT DOCUMENTS
5,380,855 A    1/1995 McGhee et al.

OTHER PUBLICATIONS

Birkofer L, Krebs K; N, N-Disubstitutierte Carbamoyl-und Thiocarbamoylchloride ueber Silyl-Derivate; Tetrahedron Letters; 1968; 7; 885-888.
Knausz D et al; Trimethylsilylated N-alkyl-substituted carbamates I. preparation and some reactions; Journal of Organometallic Chemistry; 1983; 256/1; 11-21, 12, 13 table 1 compounds 1-6, 19 and 15.
McGhee, Williams, et al. Conversion of amines to carbamoyl chlorides. Tetrahedron Letters, 1994, vol. 35(6), pp. 839-842.

*Primary Examiner* — Rebecca Anderson
*Assistant Examiner* — Samantha Shterengarts
(74) *Attorney, Agent, or Firm* — J. Scott Young

(57) ABSTRACT

The present invention relates to a new and useful process for preparing N,N-substituted carbamoyl halides from secondary amines, carbon dioxide, trialkylsilyl chloride and a halogenating agent.

11 Claims, No Drawings

PROCESS FOR PREPARING N, N-SUBSTITUTED CARBAMOYL HALIDES

RELATED APPLICATIONS

This Application is a filed pursuant to 35 U.S.C. §371 as a U.S. National Phase Application of International Application No. PCT/EP2006/010437, filed 26 Oct. 2006, which claims priority to GB0522061.1, filed 28 Oct. 2005.

The present invention relates to a process for preparing N,N-substituted carbamoyl halides. Particularly, the invention relates to a new and useful process for preparing N,N-substituted carbamoyl halides from secondary amines, carbon dioxide, trialkylsilyl chloride and a halogenating agent.

Carbamoyl halides, particularly carbamoyl chlorides, are useful intermediates in the preparation of unsymmetrical ureas and N,N-dialkyl carbamate esters. Carbamoyl chlorides are useful intermediates in the preparation of amides in direct Friedel-Crafts acylation of aromatics.

Commercially, the phosgenation of ammonia and amines is by far the most widely used method for producing carbamoyl chlorides. For the preparation of N,N-substituted carbamoyl chlorides, the commercial process involves the phosgenation of secondary amine. The use of phosgene, however, has several disadvantages. The phosgenation route is long, energy intensive and requires handling highly corrosive materials, e.g. hydrogen chloride and chlorine, and highly toxic reagents and intermediates, e.g. phosgene and chlorine. Furthermore, the phosgenation route requires use of process equipment which can withstand high temperatures and highly corrosive conditions resulting in increased capital cost.

U.S. Pat. No. 5,380,855 discloses a non-phosgene process for preparing N,N-substituted carbamoyl halides from secondary amines, carbon dioxide and a halide containing electrophilic compound.

The present invention provides a particularly advantageous process of preparing N,N-substituted carbamoyl halides.

Thus, the present invention provides a process for the preparation of N,N-substituted carbamoyl halides of formula (I) $NH(R_1)(R_2)C(O)X$, wherein X is bromine or chlorine, which comprises:

(a) contacting carbon dioxide and a secondary amine of formula (II) $NH(R_1)(R_2)$ wherein $R_1$ and $R_2$ are independently selected from:

$C_{1-18}$ alkyl optionally substituted by halogen, cyano, nitro, aryl (optionally substituted by one or more halogen, $C_{1-6}$alkyl, $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $N(R_3)(R_4)$; $C(NOR_5)R_6$, $N(R_3)C(O)(R_4)$, $N(R_3)S(O)_2(R_4)$, $C(O)R_7$, $C(O)OR_7$, $C_{1-18}$ alkenyl optionally substituted by halogen, cyano, nitro, aryl (optionally substituted by one or more halogen, $C_{1-6}$alkyl, $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $N(R_3)(R_4)$; $C(NOR_5)R_6$, $N(R_3)C(O)(R_4)$, $N(R_3)S(O)_2(R_4)$, $C(O)R_7$, $C(O)OR_7$, $C_{1-18}$ alkoxy optionally substituted by halogen, cyano, nitro, aryl (optionally substituted by one or more halogen, $C_{1-6}$alkyl, $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$, $C_{3-7}$ cycloalkyl optionally substituted by halogen, cyano, nitro, aryl (optionally substituted by one or more halogen, $C_{1-6}$ alkyl optionally substituted by aryl (optionally substituted by one or more halogen, $C_{1-6}$alkyl or $CF_3$), $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$, Aryl optionally substituted by halogen, cyano, nitro, aryl (optionally substituted by one or more halogen, $C_{1-6}$ alkyl optionally substituted by aryl (optionally substituted by one or more halogen, $C_{1-6}$alkyl or $CF_3$), $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$, a bicyclic 6,5 or 6,6 aromatic or heteroaromatic group optionally substituted by halogen, cyano, nitro, aryl (optionally substituted by one or more halogen, $C_{1-6}$ alkyl optionally substituted by aryl (optionally substituted by one or more halogen, $C_{1-6}$alkyl or $CF_3$), $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$, a 5 or 6 membered heterocyclic ring optionally substituted by halogen, cyano, nitro, aryl (optionally substituted by one or more halogen, $C_{1-6}$ alkyl optionally substituted by aryl (optionally substituted by one or more halogen, $C_{1-6}$alkyl or $CF_3$), $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$ or $R_1$ and $R_2$ together with nitrogen to which they are attached form a 4-, 5-, 6- or 7-membered azacyclic group optionally containing one additional O, N or S atom in the azacycle, wherein such 4-, 5-, 6- or 7-membered azacyclic are optionally substituted by halogen, cyano, nitro, aryl (optionally substituted by one or more halogen, $C_{1-6}$alkyl or $CF_3$), $CF_3$, cyano, hydroxy, $C_{1-6}$alkanoyl, or $C_{1-6}$alkoxy), $C_{1-6}$alkanoyl, $C_{1-6}$alkylthio, $C(O)N(R_3)(R_4)$, $C(O)N(R_3)C_{1-6}$alkoxy, $S(O)_2N(R_3)(R_4)$, $C(NOR_5)R_6$, $N(R_3)C(O)(R_4)$, $N(R_3)S(O)_2(R_4)$, $C(O)R_7$, $C(O)OR_7$;

$R_3$ and $R_4$ are independently hydrogen, $C_{1-6}$alkyl, aryl, $C_{3-7}$ cycloalkyl, $C_{3-7}$ cycloalkyl$C_{1-6}$alkyl or $NR_3R_4$ together with N or form a 4-, 5-, 6- or 7-membered azacyclic group optionally containing one additional O, N or S atom in the azacycle and optionally substituted by halogen, cyano, nitro, aryl (optionally substituted by one or more halogen, $C_{1-6}$alkyl or $CF_3$), $CF_3$, cyano, hydroxy, $C_{1-6}$alkanoyl, or $C_{1-6}$alkoxy, $C_{1-6}$alkanoyl, $C_{1-6}$alkylthio;

$R_5$ is $C_{1-4}$alkyl, $C_{3-7}$cycloalkyl$C_{1-6}$alkyl, or $C_{3-7}$cycloalkyl;

$R_6$ is hydrogen, halogen, cyano, $C_{3-7}$cycloalkyl$C_{1-6}$alkyl, or $C_{3-7}$cycloalkyl or $C_{1-6}$alkyl;

$R_7$ is hydrogen, $C_{1-6}$alkyl or halo$C_{1-6}$alkyl;

in the presence of an organic solvent and a base under conditions of time and temperature sufficient to produce the corresponding carbamate salt(II) $(R_1)(R_2)NC(O)O-$ (b) reacting the carbamate salt (III) with trialkylsilylchloride under conditions of time and temperature sufficient to produce the corresponding trialkylsilylester carbamic acid (III) $(R_1)(R_2)NC(O)OSi(Alkyl)_3$ and (c) reacting the trialkylsilylester carbamic acid (IV) with a halogenating agent under reaction conditions of time and temperature sufficient to produce the corresponding N, N-substituted carbamoyl halide of formula (I) $(R_1)(R_2)NC(O)X$ wherein X is bromine or chlorine.

The process according to the invention provides a more efficient synthesis to prepare N,N-substituted carbamoyl halides with improved yield and avoiding the phosgenation route.

The term "bicyclic 6,5 or 6,6 aromatic or heteroaromatic group" refers to stable bicyclic aromatic groups having 9 or 10 carbon atoms in total, as well as stable bicyclic heteroaromatic groups having 9 or 10 atoms in total and containing 1 to 4 heteroatoms selected from oxygen, nitrogen and sulphur. Examples of bicyclic 6,5 or 6,6 aromatic groups include naphthyl, 5,6,7,8-tetrahydronaphthyl and 2,3-dihydroindene. Examples of bicyclic 6,5 or 6,6 heteroaromatic groups include indolyl, quinolyl, quinazolinyl, 2,3-dihydrobenzodioxinyl, isoquinolyl, benzofuranyl, benzothienyl, benzimidazolyl, indazolyl, 4-, 5-, 6- or 7-azaindolyl, benzothiazolyl, benzoxazolyl, benzisoxazolyl, benzisothiazolyl, quinoxalinyl and cinnolinyl.

Where used herein the term naphthyl, whether alone or as part of another group, is intended, unless otherwise stated, to denote both 1-naphthyl and 2-naphthyl groups.

The term "5 or 6 membered heterocyclic ring" refers to a 5 or 6-membered heterocyclic group which is partially or fully saturated. Examples of 5 or 6 membered heterocyclic rings containing at least one nitrogen and optionally containing 1 to 3 additional heteroatoms selected from oxygen, nitrogen and sulphur which are fully saturated include pyrrolidinyl, 4-oxo-piperidinyl, imidazolidinyl, pyrazolidinyl, piperidinyl, piperazinyl, morpholinyl, oxadiazolinyl, and thiomorpholinyl. Examples of 5 or 6 membered heterocyclic rings containing at least one nitrogen and optionally containing 1 to 3 additional heteroatoms selected from oxygen, nitrogen and sulphur which are partially saturated include oxazolinyl, isoxazolinyl, imidazolinyl, pyrrolinyl, and pyrazolinyl.

The term "aryl", whether alone or as part of another group, is intended, unless otherwise stated, to denote an aromatic carbocyclic ring or heteroaromatic ring such as phenyl, pyrrolyl, imidazolyl, pyrazolyl, oxadiazolyl, isothiazolyl, thiazolyl, thiazinyl, furyl, thienyl, pyridyl, pyridazinyl, pyrimidinyl, azepinyl or naphthyl, optionally substituted by one or more halogen, $C_{1-6}$alkyl, $CF_3$, cyano, hydroxy, $C_{1-6}$alkanoyl, or $C_{1-6}$alkoxy.

The term "$C_{1-18}$alkyl", whether alone or part of another group, refers to alkyl groups having from one to eighteen carbon atoms, in all isomeric forms, including methyl, ethyl, propyl, isopropyl, butyl, isobutyl, sec-butyl, tert-butyl, pentyl, neopentyl, sec-pentyl, n-pentyl, isopentyl, tert-pentyl and hexyl and the like.

The term "$C_{1-18}$ alkenyl", whether alone or part of another group, refers to an alkyl radical having one or more double bonds and containing 2 to 18 carbon atoms.

The term "$C_{1-18}$alkoxy" refers to a straight chain or branched chain alkoxy (or "alkyloxy") group having from one to eighteen carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tert-pentoxy, hexoxy and the like.

The term "$C_{3-7}$cycloalkyl" refers to a non-aromatic monocyclic carbocyclic ring having from 3 to 7-carbon atoms (unless a different number of atoms is specified) and no carbon-carbon double bonds. "Cycloalkyl" includes by way of example cyclopropyl, cyclobutyl, cyclopentyl, cyclohexyl, cycloheptyl.

When $R_1$ and $R_2$ together with nitrogen to which they are attached form a 4-, 5-, 6- or 7-membered azacyclic group optionally containing one additional O, N or S atom in the azacycle, examples of such azacyclic groups include by way of the example aziridinyl, azetidinyl, pyrrolidinyl, imidazolidinyl, pyrazolidinyl, isothiazolidinyl, thiazolidinyl, pyrrolyl, pyrrolinyl, pyrazolinyl, imidazolyl, pyrazolyl, triazolyl, tetrazolyl, piperidinyl, 4-oxo-piperidinyl, piperazinyl, morpholinyl, thiazinanyl, azepinyl and azepanyl.

In one embodiment, $R_1$ and $R_2$ are independently $C_{1-6}$ alkyl optionally substituted by aryl (optionally substituted by one or more halogen, $C_{1-6}$alkyl or $CF_3$) or $R_1$ and $R_2$ together with nitrogen to which they are attached form a 4-oxo-piperidinyl or a piperazinyl which are optionally substituted by aryl (optionally substituted by one or more halogen, $C_{1-6}$ alkyl or $CF_3$).

In one embodiment, $R_1$ and $R_2$ are independently $C_{1-6}$ alkyl optionally substituted by phenyl (optionally substituted by one or more halogen, $C_{1-6}$alkyl or $CF_3$) or $R_1$ and $R_2$ together with nitrogen to which they are attached form a 4-oxo-piperidinyl or a piperazinyl which are optionally substituted by phenyl (optionally substituted by one or more halogen, $C_{1-6}$ alkyl or $CF_3$).

In a further embodiment the secondary amine is [1-(3,5-bis-trifluoromethyl phenyl)-ethyl]methyl amine or enantiomers thereof.

In a further embodiment the secondary amine is [1-(R) 3,5-bis-trifluoromethyl phenyl)-ethyl]methyl amine.

In a further embodiment the secondary amine is 2-(4-Fluoro-2-methyl -phenyl)piperidine-4-one or enantiomers thereof.

In a further embodiment the secondary amine is 2-R-(4-Fluoro-2-methyl -phenyl)-piperidine-4-one.

Examples of N,N-substituted carbamoyl halides produced by the process of the invention include:
N-3,5 trifluoromethylphenyl, N methyl carbamoyl chloride,
2-(4-fluoro-2-methylphenyl)-4-oxo-1-piperidine carbonylchloride or enantiomers thereof.

Further Examples of N,N-substituted carbamoyl halides produced by the process of the invention include:
N,N-dibutyl carbamoyl bromide,
piperidine carbamoyl chloride,
piperidine carbamoyl bromide,
N,N-dipropyl carbamoyl chloride,
N,N-dipropyl carbamoyl bromide,
N-phenyl, N-ethyl carbamoyl chloride or
N-phenyl, N-ethyl carbamoyl bromide.

The carbamate salt is prepared in solution in the presence of a base.

Examples of organic bases which may be used in the reaction include trietylamine, pyridine, imidazole, 2,6 lutidine diethyl, isopropylamine, trimethylamine, diethyl isopropylamine, piperidine, dibutylamine, diisopropylamine, phenyl ethylamine, ethyl butylamine, ethyl butylamine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU) and the like, and mixtures of any two or more thereof.

In one embodiment of the invention the base is a mixture of triethylamine and pyridine in a volume ratio ranging from 1:1 to 3:1.

Example of inorganic base include those of alkali metals and alkaline earth metals such as sodium hydroxy, potassium hydroxy, lithium hydroxy and the like, and mixtures of any two or more thereof.

Example of organic solvents for use in the process of the invention are aprotic organic solvents. Both polar and non-polar aprotic organic solvents, as well as mixtures thereof, may be used in the process of the invention. As utilized herein, the phrase "polar aprotic organic solvent" means an aprotic organic solvent having a dielectric constant measured at 25° C. of greater than about 10 as reported in Reichardt, C., "Solvents and solvent effects in organic chemistry," 2nd ed., VCH Verlagsgesellschaft, Weinheim, (1988), Table A-1. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, ethyl acetate, toluene, tetrahydrofuran, o-dichlorobenzene, triethylamine and the like, and mixtures thereof.

Currently preferred non-polar aprotic organic solvents include ethyl acetate, dichloromethane and toluene.

Examples of polar aprotic organic solvents which can be employed in the process of the invention include N,N-dimethyl formamide, N-methyl-2-pyrrolidone, N,N-dimethyl acetamide, dimethyl sulfoxide, acetonitrile, sulfolane, pyridine and the like, and mixtures thereof.

Currently preferred polar aprotic organic solvents include acetonitrile and N,N-dimethyl formamide.

Although not specifically required, it is preferred to utilize the same solvent to carry out all reaction steps of the present invention in order to avoid additional process equipment for recovering additional solvents.

The amount of solvent utilized in the process of the invention is preferably at least the amount necessary to solubilize the carbamate salt present.

In one embodiment the solvent of the process of the invention is ethylacetate which may contain ethanol up to 0.25% vol/vol.

Trialkylsilyl chloride compounds useful for use in the process include trimethylsilyl chloride, triethylsilyl, tert-butylmethylsilyl.

In one embodiment of the invention trialkylsilylchloride is trimethylsilyl chloride.

Applicable halogenating agents for use in the process of the invention include $POX_3$, $PX_3$, $PX_5$, $SOX_2$, $SO_2X_2$, $CO_2X_2$ and mixtures thereof where X is bromine or chlorine.

Examples of a suitable halogenating agent include $POCl_3$, $POBr_3$, $PCl_3$, $PBr_3$, $PCl_5$, $PBr_5$, $SOCl_2$, $CO_2Cl_2$, $SOBr_2$, $SO_2Cl_2$ and $SO_2Br_2$.

In one embodiment of the invention the halogenating agent is $SOCl_2$ or $CO_2Cl_2$.

The reaction between the secondary amine and carbon dioxide is conducted under a $CO_2$ atmosphere. The pressure of $CO_2$ during this reaction is from 1 to 1.5 Bar (atmospheric pressure). It is preferred to charge the $CO_2$ to the reaction vessel containing the secondary amine below the liquid level in the reaction vessel.

In one embodiment the reaction of carbamate salt with trialkyl silyl chloride and successively with the halogenating agent is conducted under a $CO_2$ atmosphere.

In a further embodiment, the reaction of carbamate salt with and successively with the halogenating agent can be conducted under any inert atmosphere, e.g. nitrogen, argon or air, provided the atmosphere is substantially dry. A substantially dry atmosphere is desired because water will react with the halogenating agent.

The temperature and time used in the process of the invention will depend on the particular reaction involved. For the reaction of secondary amine with $CO_2$, the temperature is about −78° C. to about 50° C., preferably about −20° C. to about 30° C., and most preferably about 20° C. to about 30° C. The time will broadly be the time required to achieve complete mixing of reactants to about 6 hours, preferably about 5 minutes to about 2 hours, and most preferably about 15 minutes to about 60 minutes. For the reaction of a carbamate salt with a trialkylsilylchloride compound, the temperature is about −78° C. to about 25° C., preferably about −40° C. to 25° C., and most preferably about −20° C. to about 25° C.

For the reaction of trialkylsilyl esters of carbamic acid with a halogenating agent the temperature is about −78° C. to about 40° C., preferably about −40° C. to 25° C., and most preferably about 0° C. to about 25° C.

The time will broadly be the time required to achieve complete mixing of the reactants to about 4 hours, preferably about 1 minute to about 2 hours, and most preferably about 5 minutes to about 60 minutes.

In one embodiment of the invention the amine is [1-(R) 3,5-bis-trifluoromethyl phenyl)-ethyl]methyl amine, the solvent is ethylacetate containing ethanol up to 0.25% vol/vol, the halogenating agent is $SOCl_2$, the trialkylsilylchloride is trimethylsilylchloride, the base is a mixture of triethylamine and pyridine in a volume ratio ranging from 1:1 to 3:1.and the reaction temperature is in the range 20-25° C.

In one embodiment of the invention the amine is 2-R-(4-Fluoro-2-methyl -phenyl)piperidine-4-one, the solvent is ethylacetate containing ethanol up to 0.25% vol/vol, the halogenating agent is $SOCl_2$, the trialkylsilylchloride is trimethylsilylchloride, the base is a mixture of triethylamine and pyridine in a volume ratio ranging from 1:1 to 3:1.and the reaction temperature is in the range 0°-25° C.

The desired N,N-substituted carbamoyl halides produced by the process of the invention can be recovered by any conventional means known in the art, such as that disclosed in the example herein. Alternatively N,N substituted carbamoyl halides obtained according to the process of the invention may be used without being isolated in a further reaction.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The following example is intended for illustration only and is not intended to limit the scope of the invention in any way, the invention being defined by the claims which follow.

In the Example, Proton Magnetic Resonance (NMR) spectra were recorded on Varian instruments at 300, 400 or 500 MHz, on Bruker instrument at 300 MHz, chemical shifts are reported in ppm (δ) using the residual solvent line as internal standard. Splitting patterns are designed as s, singlet; d, double; t, triple; q, quartet; m, multiplet; b, broad. The NMR spectra were recorded at temperature ranging from 25 to 90° C.; when more than one conformer were detected the chemical shifts for the most abundant one is reported. High Performance Liquid Chromatography (HPLC) spectra were acquired with Agilent Technology HP 1200 LC system equipped with a Luna (50×2 mm, 3 μl) as column; DAD UV chromatographic traces are typically taken on PDA detector; the method used a gradient 0-95% B in 8 minutes, with Mobile phase A: Water+0.05% TFA; Mobile Phase B: Acetonitrile+0.05% TFA and a flow of 1.0 ml/min and a temperature of 40° C.; X=220 nm Liquid Chromatography Mass Spectroscopy (LC-MS) data were obtained by using a Agilent LC/MSD 1100 Mass Spectrometer, operating in ES (+) and ES (−) electrospray ionization mode coupled with HPLC instrument Agilent 1100 Series (described above).

EXAMPLE 1

N-[1-(R) 3,5-bis-trifluoromethyl phenyl)-ethyl]-N-methyl carbamoyl chloride

[1-(R) 3,5-bis-trifluoromethyl phenyl)-ethyl]methyl amine L(−)maleate (13.5 g; 33.33 mmol) was suspended in ethyl acetate (39.9 ml) and ethanol (0.1 ml); aqueous sodium carbonate 13% (40 ml) was added and the mixture was stirred at a temperature 20-25° C. until a clear solution was formed. The water phase was discarded and the organic phase was washed with water (40 ml). Fresh ethyl acetate (49.87 ml) and ethanol (0.13 ml) were added, the solution was concentrated to 40 ml, a second amount of fresh ethyl acetate (49.87 ml) and ethanol (0.13 ml) was added and the solution was concentrated to 40 ml. Fresh ethyl acetate (109.7 ml) and ethanol (0.3 ml) were added under $CO_2$ flow. A cycle of vacuum and $CO_2$ in the vessel was applied, then $CO_2$ was maintained for 10 minutes. Then, a neat $Et_3N$ (6.1 ml; 46.34 mmol) was added and the reaction mixture was stirred at a temperature 20-25° c. for 30 minutes. Trimethylmethylsilylchloride (6.4 ml; 40.42 mmol) was added in 30 minutes (exothermic step) and the reaction mixture was stirred for further 30 minutes at room temperature. Pyridine (5.4 ml; 66.66 mmol) was added, then $SOCl_2$ (3.6 ml; 40.42 mmol) was added in 10 minutes. The reaction mixture was stirred at room temperature for 10 hours under $CO_2$ atmosphere. 13% w/w aqueous racemic malic acid (60 ml) was added and the mixture was stirred for 15 minutes; the water phase was discarded then the organic phase was washed with water (60 ml); the water phase was discarded then the organic phase was washed with sodium carbonate 13% w/w (60 ml). Finally, the water phase was discarded and ethyl acetate (49.87 ml) and ethanol (0.13 ml) were added and the solution was concentrated to 50 ml; further ethyl acetate (49.87 ml) and ethanol (0.13 ml) were added and the solution was concentrated to dryness to give the title compound as a pale yellow (10.41 gr; 31.33 mmol 94% yield)

NMR-($d_6$-DMSO) δ (ppm)

8.04 δ (br s, 1H), 7.97 δ (br s, 2H), 5.52 δ (q, 1H), 2.97 δ (s, 3H), 1.66 δ (d, 3H)

EXAMPLE 2

(2R)-2-(4-fluoro-2-methylphenyl)-4-oxo-1-piperidinyl carbonyl; chloride (2R)-2-(4-fluoro-2-methylphenyl)-4-oxo-1-piperidine L(−) mandelate (2 g; 5.57 mmol) was suspended in ethyl acetate (8 ml); aqueous sodium carbonate 13% w/w (10 ml) was added and the mixture was stirred at a temperature 20-25° C. until a clear solution was formed.

The water phase was discarded and the organic phase was washed with aqueous sodium chloride 10% w/w (4 ml). Fresh ethyl acetate (8 ml) were added, the solution was concentrated to 6 ml, a second amount of fresh ethyl acetate (8 ml) was added and the solution was concentrated to 6 ml.

Fresh ethyl acetate (2 ml) and neat $Et_3N$ (1.94 ml; 13.92 mmol) were added under $CO_2$ flow at 0° C. The mixture was stirred for 10 minutes, then Trimethylmethylsilylchloride (1.42 ml; 11.14 mmol) was added in 5 minutes (exothermic step) and the reaction mixture was stirred for further 30 minutes at 0° C. Pyridine (0.58 ml; 7.24 mmol) was added, then $SOCl_2$ (0.53 ml; 7.24 mmol) was added in 5 minutes. The reaction mixture was stirred at 0° C. for 1 h, then at a temperature 20-25° C. for 5 hours under $CO_2$ atmosphere. Water (20 ml) was added was added; the water phase was discarded then the organic phase was washed with sodium carbonate 13% w/w (20 ml); the water phase was discarded then the organic phase was dried on sodium sulphate. The organic phase was filtered and concentrated to dryness to give the title compound as a pale yellow (1.5 gr; 5.57 mmol 100% yield)

HPLC Rt: 2.33 min; MS: [H+] 270

The invention claimed is:

1. A process for preparing N,N-substituted carbamoyl halides of formula (I) $(R_1)(R_2)NC(O)X$ wherein X is bromine or chlorine, and R1 is 1-(3,5-bis-trifluoromethyl phenyl)-ethyl, R2 is methyl, or R1 and R2, together with the nitrogen to which they are attached, form 2-(4-Fluoro-2-methyl-phenyl)-piperidine-4-one, which comprises the following steps:
 a) contacting carbon dioxide and a secondary amine selected from [1-(3,5-bis-trifluoromethyl phenyl)-ethyl] methyl amine, 2-(4-Fluoro-2-methyl-phenyl)piperidine-4-one and enantiomers thereof
 in the presence of an organic solvent and a base under conditions of time and temperature sufficient to produce the corresponding carbamate salt (III) $(R_1)(R_2)NC(O)O—$
 (b) reacting the carbamate salt (III) with trialkylsilylchloride under conditions of time and temperature sufficient to produce the corresponding trialkylsilylester carbamic acid (IV) $(R_1)(R_2)NC(O)OSi(Alkyl)_3$ and
 (c) reacting the trialkylsilylester carbamic acid (IV) with a halogenating agent under reaction conditions of time and temperature sufficient to produce the corresponding N,N-substituted carbamoyl halide of formula (I) $(R_1)(R_2)NC(O)X$ wherein X is bromine or chlorine.

2. The process according to claim 1 wherein the secondary amine is [1-(R) 3,5-bis-trifluoromethyl phenyl)-ethyl]methyl amine.

3. The process as claimed in claim 1 wherein said organic solvent is a non-polar aprotic solvent.

4. The process as claimed in claim 1 wherein the organic solvent is ethylacetate which may contain ethanol up to 0.25% vol/vol.

5. The process as claimed in claim 1 wherein said base is an organic base.

6. The process as claimed in claim 5 wherein the organic base is a mixture of triethylamine and pyridine in a volume ratio ranging from 1:1 to 3:1.

7. The process as claimed in claim 1 wherein the trialkylsilylchloride is trimethylsilylcholoride.

8. The process as claimed in claim 1 wherein the halogenating agent is $SOCl_2$ or $CO_2Cl_2$.

9. A process according to claim 1 wherein
 the secondary amine is 2-R-(4-Fluoro-2-methyl-phenyl) piperidine-4-one,
 the organic solvent is ethylacetate which may contain ethanol up to 0.25% vol/vol,
 the halogenating agent is $SOCl_2$,
 the trialkylsilylchloride is trimethylsilylchloride, the base is a mixture of triethylamine and pyridine in a volume ratio ranging from 1:1 to 3:1, and the reaction temperature is in the range 0°-25° C.

10. A process according to claim 1 wherein the secondary amine is [1-(R) 3,5-bis-trifluoromethyl phenyl)-ethyl]methyl amine, the organic solvent is ethylacetate which may contain ethanol up to 0.25% vol/vol, the halogenating agent is $SOCl_2$, the trialkylsilylchloride is trimethylsilylchloride, the base is a mixture of triethylamine and pyridine in a volume ratio ranging from 1:1 to 3:1, and the reaction temperature is in the range 20°-25° C.

11. The process according to claim 1, wherein the secondary amine is 2-R-(4-Fluoro-2-methyl-phenyl)-piperidine-4-one.

* * * * *